United States Patent
Heng

(10) Patent No.: US 9,068,916 B2
(45) Date of Patent: Jun. 30, 2015

(54) MICROASSEMBLED IMAGING FLOW CYTOMETER

(75) Inventor: Xin Heng, Emeryville, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 381 days.

(21) Appl. No.: 13/039,990

(22) Filed: Mar. 3, 2011

(65) Prior Publication Data
US 2011/0222051 A1  Sep. 15, 2011

Related U.S. Application Data

(60) Provisional application No. 61/314,056, filed on Mar. 15, 2010.

(51) Int. Cl.
*G06K 9/00* (2006.01)
*G01N 15/14* (2006.01)
*G01N 21/64* (2006.01)

(52) U.S. Cl.
CPC .......... *G01N 15/147* (2013.01); *G01N 15/1475* (2013.01); *G01N 15/1484* (2013.01); *G01N 21/6428* (2013.01); *G01N 2015/149* (2013.01)

(58) Field of Classification Search
USPC ........... 356/338, 441, 442, 436; 382/128, 133
See application file for complete search history.

(56) References Cited

U.S. PATENT DOCUMENTS

| 5,457,526 | A | 10/1995 | Kosaka |
| 5,717,519 | A | 2/1998 | Sugiyama et al. |
| 7,671,987 | B2 * | 3/2010 | Padmanabhan et al. ...... 356/338 |
| 2003/0227609 | A1 * | 12/2003 | Oskotsky et al. ............... 355/67 |
| 2005/0094261 | A1 | 5/2005 | Hell et al. |
| 2005/0122522 | A1 | 6/2005 | Padmanabhan et al. |
| 2007/0188737 | A1 | 8/2007 | Fritz |
| 2008/0151240 | A1 | 6/2008 | Roth |

(Continued)

FOREIGN PATENT DOCUMENTS

| CN | 101278829 A | 10/2008 |
| EP | 2034291 A1 | 3/2009 |

(Continued)

OTHER PUBLICATIONS

Bewersdorf et al., "Multifocal Multiphoton Microscopy," Optics Letters, May 1, 1998, pp. 655-657, vol. 23, No. 9, Optical Society of America.
International Search Report and Written Opinion of PCT/US2011/28538 mailed on May 9, 2011, 8 pages.

(Continued)

*Primary Examiner* — Rebecca C Bryant
(74) *Attorney, Agent, or Firm* — Kilpatrick Townsend & Stockton LLP

(57) ABSTRACT

A microassembled imaging cytometer includes a sensing location that undergoes relative motion with a cell. Light from a light source is focused by a focusing element to a plurality of focused illumination spots or lines at the sensing location, illuminating the cell as the cell traverses the sensing location. A collection lens collects light emanating from the cell and refocuses the collected light onto an array light sensor. The focusing element may include an array of microlenses having spherical or aspheric surfaces. The system may include a processing unit that constructs a digital image of the cell based at least in part on signals produced by the array light sensor indicating the intensity and distribution of light falling on the array light sensor. The system may characterize cells using light emanating from the cells by fluorescence.

34 Claims, 12 Drawing Sheets

(56) References Cited

U.S. PATENT DOCUMENTS

| | | |
|---|---|---|
| 2009/0027666 A1 | 1/2009 | Godin et al. |
| 2009/0225411 A1 | 9/2009 | Cui et al. |
| 2010/0021039 A1 | 1/2010 | Ortyn et al. |
| 2010/0309457 A1 | 12/2010 | Cui et al. |
| 2011/0085219 A1 | 4/2011 | Yang et al. |
| 2011/0170105 A1 | 7/2011 | Cui et al. |
| 2011/0205339 A1 | 8/2011 | Pavani et al. |
| 2011/0205352 A1 | 8/2011 | Pavani et al. |

FOREIGN PATENT DOCUMENTS

| | | |
|---|---|---|
| JP | 06-242015 | 9/1994 |
| JP | 2003520954 A | 7/2003 |
| JP | 2006-84482 | 3/2006 |
| JP | 2008539425 A | 11/2008 |
| JP | 2009522556 A | 6/2009 |
| JP | 2009-270982 | 11/2009 |
| JP | 2009258071 | 11/2009 |
| JP | 2009258071 A | 11/2009 |
| JP | 2013522629 | 6/2013 |
| WO | 2011/047053 A2 | 4/2011 |

OTHER PUBLICATIONS

Kim et al., "Design and Fabrication of Aspheric Microlens Array for Optical Read-Only-Memory Card Systems," Japanese Journal of Applied Physics, Aug. 22, 2006, pp. 6708-6712, vol. 45, No. 8B, The Japan Society of Applied Physics.

Office Action from Japanese Application No. JP2013-500160, dated Nov. 5, 2013. English Translation Only.

Robinson, "Comparative Overview of Flow and Image Cytometry", *Current Protocols in Cytometry* (2005) 12.1.1-12.1.11 pages.

"Why use a confocal microscope?" archived Jan. 7, 2020, retrieved on Jul. 25, 2014 from: http://web.archive.org/web20100107065201/https://depts.washington.edu/keck/intro.html , 7 pages.

Office Action in related Canadian application No. 2792628 mailed on Mar. 13, 2014, 3 pages.

Office Action in related Chinese application No. 201180013809.2 issued on Mar. 5, 2014, 23 pages.

Extended European Search Report of related EP Application No. 11756866.7, issued Jul. 14, 2014, 9 pages.

Second Office Action in related Chinese Application No. 201180013809.2 issued on Nov. 14, 2014, 14 pages.

Final Office Action in related Japanese Application No. 2013-500160 issued on Nov. 4, 2014, 3 pages.

\* cited by examiner

MICROASSEMBLED IMAGING FLOW CYTOMETER

This application claims the benefit of U.S. Provisional Application No. 61/314,056 filed Mar. 15, 2010 and titled "Microassembled Confocal Imaging Flow Cytometer", the entire disclosure of which is hereby incorporated by reference herein.

BACKGROUND OF THE INVENTION

Cytometry is a technical specialty concerned with the counting and characterization of biological cells. FIG. 1 shows a simplified diagram of a system for performing a technique known as imaging flow cytometry. In a basic form of imaging flow cytometry, cells 101 are suspended in a fluid and entrained single-file in a narrow transparent tube 102. The entrainment can be accomplished by any of several methods, including hydrodynamic focusing. A light source 103 illuminates each cell 101 as it passes a measurement location. Light source 103 may be, for example, a laser. Light from light source 103 is scattered by the cell 101 being measured. Some light 105 is gathered by an objective lens 106 and redirected to form an image at a light sensor 107. Light sensor 107 may be, for example, a component of a microscope or camera. Various optical components may cooperate with objective lens 106 in directing light 105 to sensor 107, including, for example, partially reflective mirror 108 and an additional lens 109. Output signals from sensor 107 are sent to a processing unit 110, which may store and analyze the signals to discern information about each cell, for example its size and some information about its internal structure.

In some applications, a compact cytometry system may be desirable, for example for portable use, or for circulating tumor cell screening in a small clinic.

BRIEF SUMMARY OF THE INVENTION

According to one aspect, a microassembled imaging cytometer comprises a sensing location that undergoes relative motion with a cell, a light source, and a focusing element. The focusing element focuses light from the light source to a plurality of focused illumination spots at the sensing location, such that the cell is illuminated by one or more of the focused illumination spots as the cell traverses the sensing location. The cytometer further comprises an array light sensor and a collection lens that collects and refocuses light emanating from the cell onto the array light sensor. In some embodiments, the microassembled imaging cytomter further comprises a flow channel through which the cell is transported by a flowing fluid, the flow channel at least partially bounded by a wall that has at least a portion that is substantially transparent. The relative motion may result at least in part from movement of the cell. The relative motion may result at least in part from movement of a portion of the cytometer. In some embodiments, the cell is attached to a slide, and wherein the relative motion results at least in part from movement of the slide. In some embodiments, illumination of the cell is performed from a side of the sensing location, and sensing of the light emanating from the cell is performed from the same side of the sensing location. In some embodiments, illumination of the cell is performed from a side of the sensing location, and sensing of the light emanating from the cell is performed from a different side of the sensing location. The focusing element may comprise an array of microlenses having spherical surfaces. The focusing element may comprise an array of microlenses having aspheric surfaces. The focusing element may comprise at least one diffractive element. The light source may comprise a laser. In some embodiments, the array light sensor comprises an array of pixels and produces signals indicating the intensity and distribution of light falling on the pixels, and the cytometer further comprises a processing unit that constructs a digital image of the cell based at least in part on the signals. In some embodiments, the processing unit constructs the digital image of the cell in part by spatially correlating light intensity readings taken from different parts of the cell at different times. In some embodiments, correlating the light intensity readings taken from different parts of the cell at different times is performed at least in part based on a speed at which the cell traverses the sensing location. The focusing element may comprise a linear array of microlenses. The focusing element may comprise a two-dimensional array of microlenses. The array light sensor may comprise a linear array of pixels. The array light sensor may comprise a two-dimensional array of pixels. In some embodiments, the microassembled imaging cytometer further comprises at least one optical filter between the sensing location and the array light sensor. In some embodiments, the array light sensor comprises at least one sensor selected from the group consisting of a charge coupled device sensor, an electron multiplying charge coupled device sensor, an avalanche photodiode sensor, a photomultiplier tube, and a complementary metal oxide semiconductor sensor. In some embodiments, the plurality of focused illumination spots form an array of focused illumination spots, the array being skewed in relation to the motion of the cell and the sensing location. The microassembled imaging cytometer may further comprise an optical element proximate the array light sensor, the optical element configuring the microassembled imaging cytometer to be substantially confocal. The optical element may comprise an array of microapertures. The optical element may comprise a bundle of optical fibers. In some embodiments, the collection lens collects and refocuses light emanating from the cell by fluorescence.

According to another aspect, a method of performing cytometry comprises generating a light beam using a light source, focusing light from the light beam to a plurality of focused illumination spots at a sensing location that undergoes relative motion with a cell, and collecting and refocusing light emanating from the cell onto an array light sensor. The method further comprises producing signals from the array light sensor indicating the intensity and distribution of light falling on the array light sensor, and constructing, using a processing unit, a digital image of the cell based at least in part on the signals from the array light sensor. The method may further comprise converting the signals to numerical values representing a pattern of light falling the array light sensor. In some embodiments, constructing a digital image of the cell further comprises taking a time-sequenced series of readings of the light falling on the array light sensor, separately tracking light readings from the array light sensor corresponding to the individual focused illumination spots, and spatially aligning the separate light readings based at least in part on a known system geometry, a speed of travel of the cell, and a frequency at which light readings are taken. In some embodiments, the method further comprises filtering the light emanating from the cell to selectively block light in wavelengths emitted by the light source and to selectively pass light in wavelengths emanating from the cell by fluorescence. In some embodiments, the method further comprises providing an optical element proximate the array light sensor, the optical element configuring the microassembled imaging cytometer to be substantially confocal.

According to another aspect, a microassembled imaging cytometer comprises a sensing location that undergoes relative motion with a cell, a light source, and a focusing element. The focusing element focuses light from the light source to a plurality of focused illumination lines at the sensing location, such that the cell is illuminated by one or more of the focused illumination lines as the cell traverses the sensing location. The microassembled imaging cytometer further comprises a light sensor, and a collection lens that collects and refocuses light emanating from the cell onto the array light sensor. The light sensor may comprise an array of pixels.

According to another aspect, a microassembled imaging cytometer, comprises a sensing location that undergoes relative motion with a cell, a light source, and a focusing element. The focusing element focuses light from the light source to a plurality of focused illumination spots or lines at the sensing location, such that the cell is illuminated by one or more of the focused illumination spots or lines as the cell traverses the sensing location. The microassembled imaging cytometer further comprises an array light sensor, a collection lens that collects and refocuses light emanating from the cell onto the array light sensor, a processing unit that analyzes signals from the light sensor to classify a cell, and a sorting mechanism that directs the classified cell to one of at least two collection channels.

DETAILED DESCRIPTION OF THE INVENTION

Figure 1:
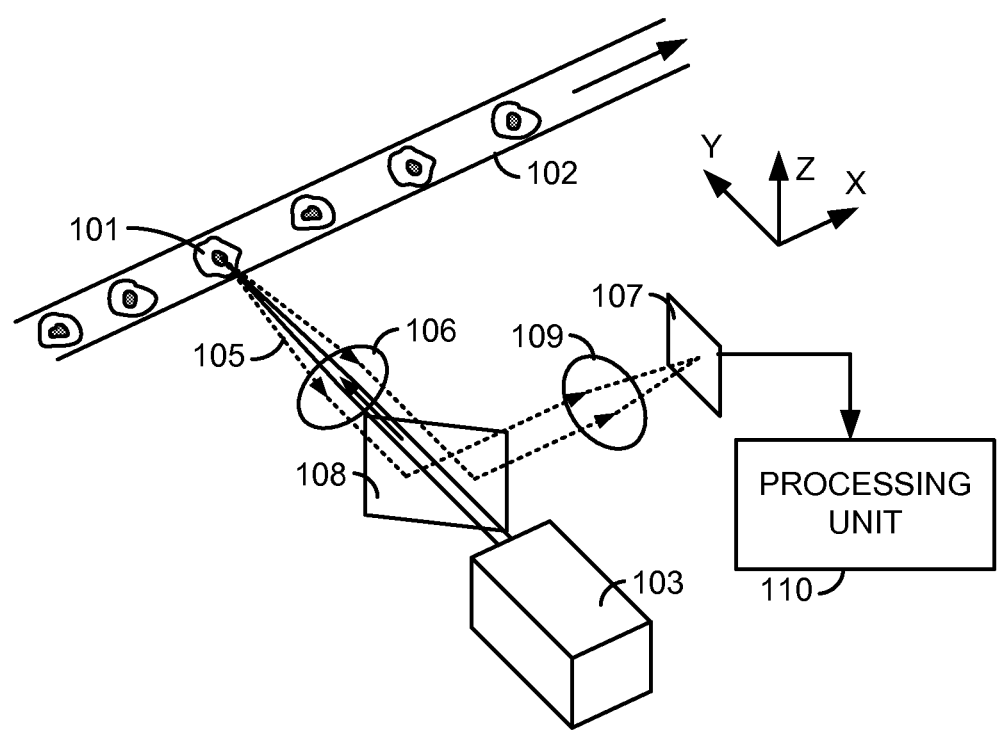
FIG. 1 shows a simplified diagram of a system for performing imaging flow cytometry.
Figure 2:
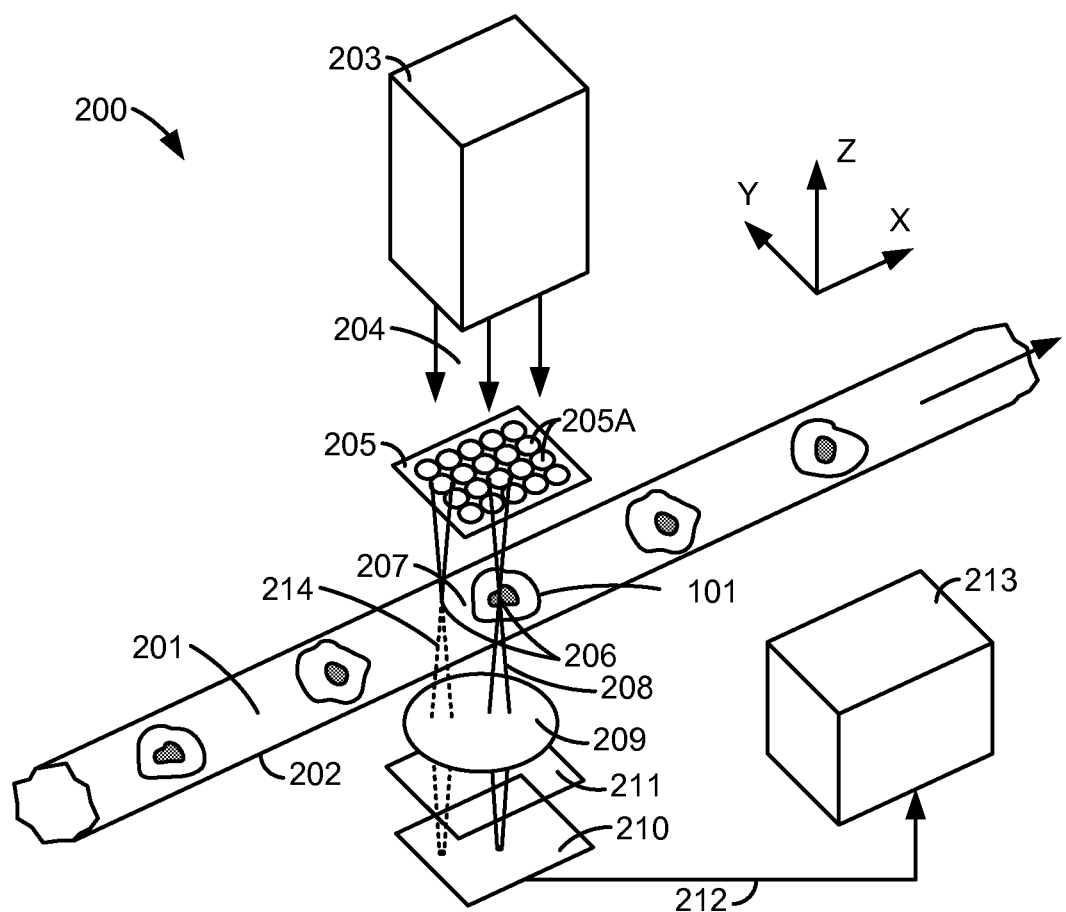
FIG. 2 illustrates a schematic oblique view of a microassembled imaging cytometer according to embodiments of the invention.

FIG. 2 illustrates a schematic oblique view of a microassembled imaging cytometer 200 according to embodiments of the invention. FIG. 2 is not necessarily drawn to scale, and some parts may be omitted or simplified for clarity.

For the purposes of this disclosure, the term "microassembled" means to be assembled using components, equipment, and techniques that enable assembly of very small structures with assembly tolerances much smaller than those achievable with conventional machine tools and assembly techniques. For example individual components may have functional features or dimensions on the order of 5 to 100 microns, and the components may be assembled together using equipment specially designed to manipulate the small components with assembly tolerances on the order of 0.1 to 10 microns. Microassembly techniques may shrink the spacing of otherwise widely separated optical or mechanical components, enabling integration and parallelism.

Microassembled imaging cytometer 200 comprises a flow channel 201, through which a cell 101 is transported in a flowing fluid. Flow channel 201 is bounded by a wall 202, which has at least a portion that is substantially transparent. The system also comprises a light source 203, which produces a beam 204 for illuminating cell 101. Beam 204 is preferably a coherent beam, and light source 203 is accordingly conveniently a laser.

A focusing element 205 receives light from light source 203 and focuses the light to a plurality of focused illumination spots 206 at a sensing location 207 within flow channel 201. As a result of the flow of cell 101 through flow channel 201, sensing location 207 and cell 101 undergo relative motion. At any one time, cell 101 may be illuminated by one or more of the illumination spots 206 as cell 101 traverses sensing location 207. In example system 200, focusing element 205 comprises a two-dimensional array of microlenses 205A, but other kinds of focusing elements could be used. For example, focusing element 205 could be a transmission or reflection hologram of an original nanoaperture array, a Fresnel zone plate array, or another kind of focusing element. Each microlens 205A may produce an illumination spot 206. (Only two illumination spots 206 are shown in FIG. 2 for clarity.) Sensing location 207 may be substantially planar, defined by the locus of the focused illumination spots 206.

When cell 101 encounters one of the focused illumination spots, light 208 emanates from cell 101. For example, cell 101 may be tagged with a fluorophore that emanates light by fluorescence when it is excited by focused light from beam 204. Alternatively, microassembled imaging cytometer 200 may perform direct imaging of cells 101 using light scattered from cell 101. At least some of the light 208 emanated from cell 101 is collected and refocused by a collection lens 209 onto an array light sensor 210. (Another light bundle 214 is shown in FIG. 2 in broken lines, indicating light that may emanate from cell 101 when cell 101 is in a different position in flow channel 201.) One or more filters such as filter 211 may be placed between sensing location 207 and array light sensor 210. For example, filter 211 may reside between flow channel 201 and lens 209, between lens 209 and array light sensor 210, or between elements of lens 209, if lens 209 includes multiple elements. Filter 211 may, for example, selectively block light in wavelengths emitted by light source 203, and selectively pass light in wavelengths emanating from cell 101 by fluorescence, so that the light reaching array light sensor 210 is substantially all generated by fluorescence. Array light sensor 210 may be, for example, a component of a digital camera, and may comprise an ordered array of light-sensitive elements, which may be referred to as pixels. Array light sensor 210, possibly under control of other electronics not shown, produces signals indicating the intensity of light falling on each pixel during a given exposure time. The signals are thus indicative of the intensity and distribution of light falling on array light sensor 210 during the exposure. These signals may be transmitted 212 to a processing unit 213 for storage, analysis, or display. The signals may be converted to digital values, for example using an analog-to-digital converter (not shown), which may reside in any convenient location in the system. Processing unit 213 may comprise a microprocessor and other electronic components, and may be, for example, a general purpose computer specially programmed to perform various analyses of the signals from array light sensor 210. As will be explained in more detail later, processing unit 213 may collect a series of digital images from array light sensor 210, taken at intervals in time, and may construct an image of cell 101 from the series of images.

Figure 3:
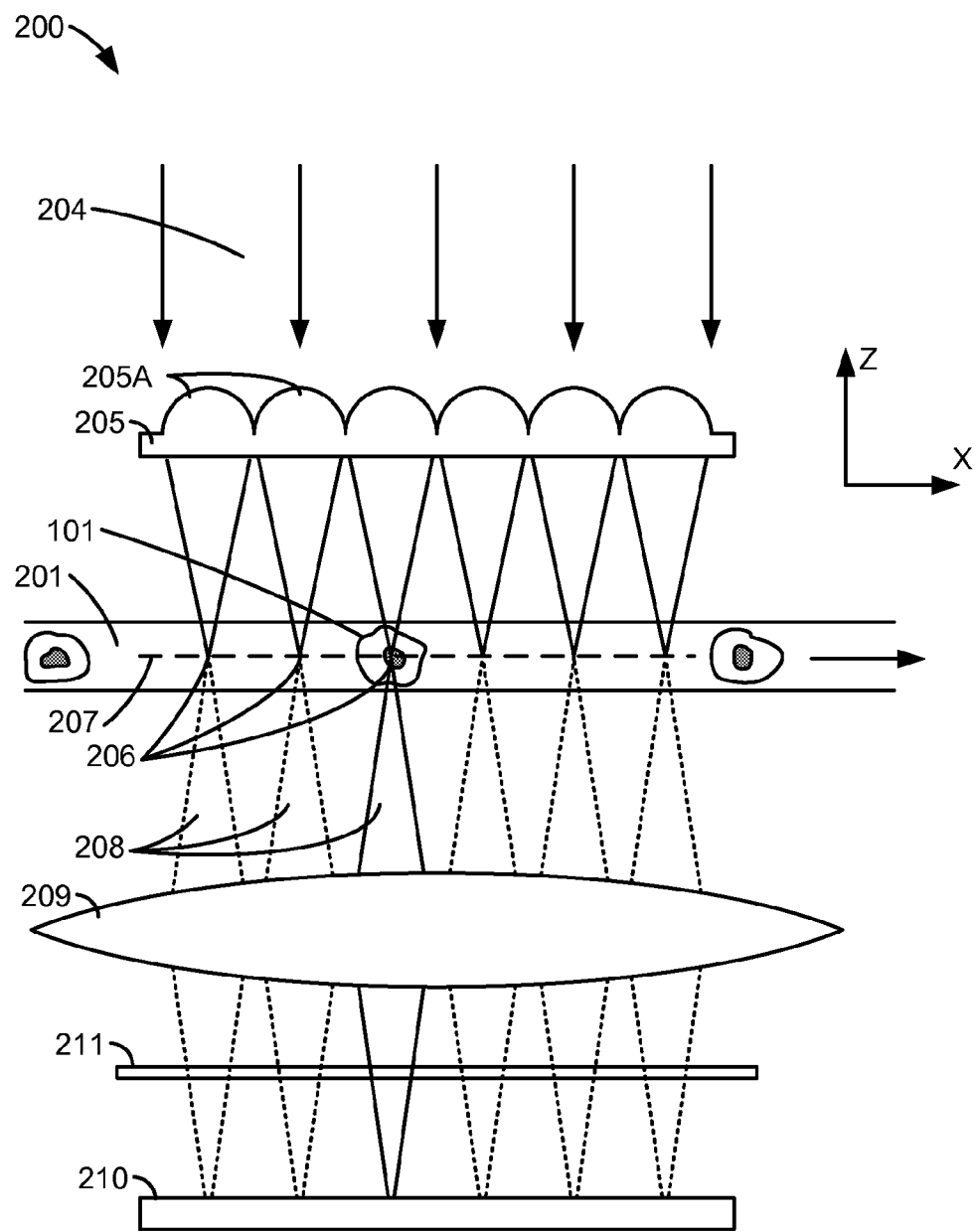
FIG. 3 illustrates an orthogonal view of a portion of the microassembled imaging cytometer of FIG. 2, according to embodiments of the invention.

FIG. 3 illustrates an orthogonal view of a portion of example microassembled imaging cytometer 200, as seen along the Y direction shown in FIG. 2. Microlenses 205A receive beam 204. Microlenses 205A may have spherical surfaces (that is, the curved surface of each microlens may be a portion of a sphere), or may preferably have aspheric surfaces in order to achieve very small spot size and high resolution. Techniques for making arrays of microlenses, including aspheric microlenses are known. See, for example, Hongmin Kim, Gibong Jeong, Young-Joo Kim, and Shinill Kang, "Design and Fabrication of Aspheric Microlens Array for Optical Read-Only-Memory Card System", *Japanese Journal of Applied Physics*, Vol. 45, No. 8B, 2006, pp. 6708-6712, the entire disclosure of which is hereby incorporated by reference. The size and spacing of microlenses 205A may be any workable values, but microlenses 205A may preferably be centered between 5 and 20 microns apart. In one example embodiment, each microlens 205A may have a diameter of about 15 microns, and microlenses 205A may be densely packed about 15 microns apart. Preferably, any interstices between microlenses 205A are made opaque, so that any light passing through focusing element 205 passes through the focusing surface of one of microlenses 205A. The distance from focusing element 205 to sensing location 207 may be, for example, about 10 to 100 microns, and preferably less than 50 microns. Systems embodying the invention may include more or fewer microlenses than are illustrated, depending on the desired pixel density of the resulting images. In some embodiments, about 200 microlenses may be used.

Each microlens 205A focuses a portion of beam 204, so that a plurality of focused illumination spots 206 is created at sensing location 207. Sensing location 207 is preferably near the center of flow channel 201, and flow channel 201 preferably constrains cells 101 to encompass sensing location 207 as cells 101 traverse flow channel 201. While system 200 may be adapted to characterize a wide variety of cells and operate at any suitable speed, a typical cell 101 may be on the order of 10 to 20 microns across, and may traverse flow channel 201 at a rate of, for example, 1 to 50 millimeters per second. The sampling resolution of the system is determined by the rate at which digital images are obtained and the velocity at which cells 101 traverse flow channel 201. The optical resolution of the system is primarily set by the size of focused illumination spots 206. Aspheric microlenses 205A may be able to achieve focus spot sizes 0.5 microns or smaller.

Light 208 emanating from cells 101 is collected by collection lens 209 and refocused onto array light sensor 210. While collection lens 209 is depicted in FIG. 3 as a simple double-convex lens, any suitable lens configuration may be used, including plano-convex, meniscus, multiple-element, or other kinds of lenses. Because the optical resolution of the system is primarily set by the size of focused illumination spots 206, the performance of collection lens 209 may not be critical, so long as the light from the various microlenses 205A is directed to separate, discernible pools on the surface of array light sensor 210. Processing unit 213 may simply sum the readings from several adjacent pixels of sensor 210 to evaluate the intensity of light 208 emanating from any particular focused illumination spot 206. In the system shown in FIG. 3, collection lens 209 is configured for unity magnification, although this is not a requirement. Collection lens 209 could be configured to project a larger or smaller image of focused illumination spots 206 onto array light sensor 210. In some embodiments, collection lens 209 could project an image magnified between 2× and 5× as compared with a unity magnification image. The distance from flow channel 201 to array light sensor 210 may be any suitable distance, but may be, for example about 5 to 15 millimeters.

Array light sensor 210 may be any suitable kind of light sensor capable of separately reading the intensity of light from the various microlenses 205A. For example, array light sensor 210 may be a charge coupled device (CCD) sensor. In a CCD sensor, an array of photosensitive sites is fabricated on a semiconductor substrate. The sites have the property that electrons are accumulated in the sites at a rate proportional to the intensity of the light falling on the sites. To take an image, the sites are cleared and exposed to light for a particular exposure time. After the exposure time has passed, the electrons from the photosensitive sites are shifted into CCD storage registers. The number of electrons in each register is then roughly proportional to the amount of light that fell on the corresponding photosensitive site during the exposure. The charges from the storage sites are shifted out of the device, and typically individually converted to voltages, which are in turn converted to numerical values, for example using an analog-to-digital converter. The array of resulting numerical values, may be called a digital image. In the case of cytometry system 200, the digital image represents the pattern of light falling during the exposure time on array light sensor 210.

Other kinds of array light sensors may also be used in embodiments of the invention, especially sensors recently developed for high sensitivity applications. For example, array light sensor 210 could include a complementary metal oxide semiconductor (CMOS) sensor, an electron multiplying charge coupled device (EMCCD) sensor, an avalanche photodiode (APD) sensor, a photomultiplier tube (PMT), or an array of APDs or PMTs. Multiple sensors may be used. For example, one discrete sensor per microlens 205A could be used.

Filter 211, if present, may be for example a dichroic filter formed by selectively coating a transparent substrate, such that light in only a particular band or bands of wavelengths is readily passed through filter 211, and light at other wavelengths is substantially blocked by filter 211. Filter 211 may be particularly useful when cytometry system 200 is used to measure light emanated from cells 101 by fluorescence. Filter 211 may be configured to substantially block light at the wavelengths contained in beam 204, but to substantially pass light in a band of wavelengths at which a fluorophore in cell 101 fluoresces.

Because the spacing of microlenses 205A may be comparable to the size of cell 101, focusing element 205 may be skewed in relation to the motion between cell 101 and the sensing location 207, to ensure that cell 101 is well covered by focused illumination spots 206 as cell 101 passes through sensing location 207.

Figure 4:
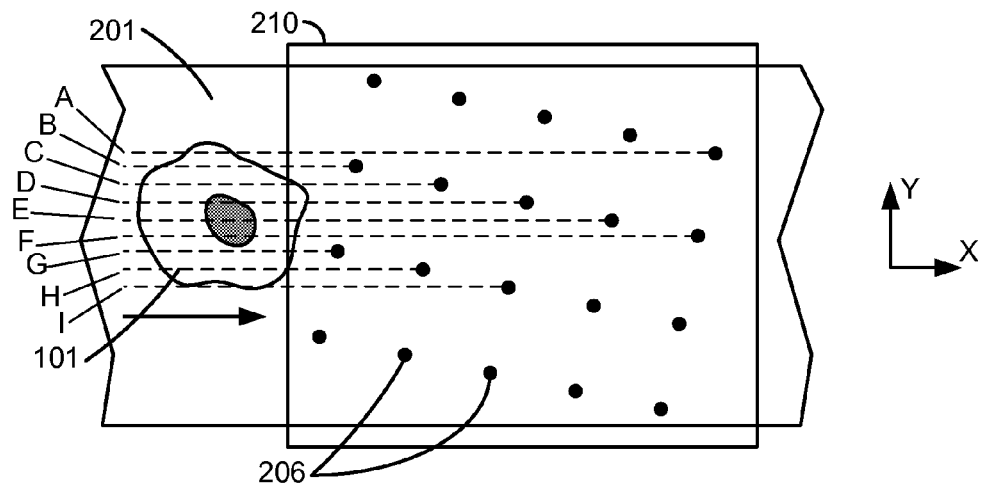
FIG. 4 shows a schematic top view of a portion of the example microassembled imaging cytometer of FIG. 2, according to embodiments of the invention.

FIG. 4 shows a schematic top view of the surface of array light sensor 210, as seen from the Z direction indicated in FIG. 2, with cell 101 and focused illumination spots 206 superimposed to illustrate the effect of skewing the array of focused illumination spots 206 with respect to flow channel 201. As can be seen in the example of FIG. 4, even though focused illumination spots 206 are relatively widely spaced with respect to each other (corresponding to the spacing of microlenses 205A), cell 101 will encounter nine different focused illumination spots as it traverses flow channel 201. These nine spots will trace closely-spaced paths A-I across cell 101, so that cell 101 is well covered during its traverse.

Figure 5A:
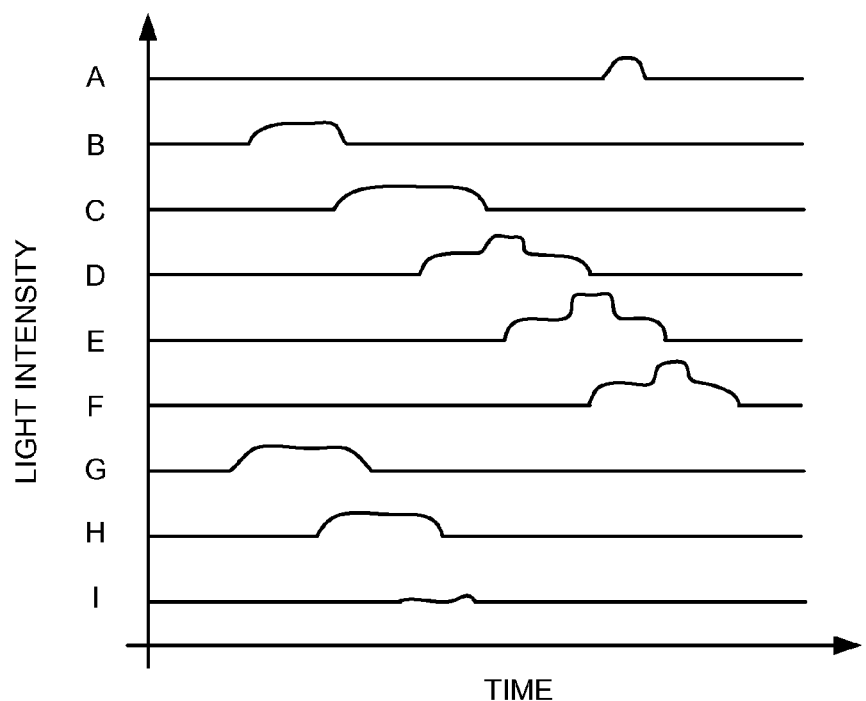
FIG. 5A illustrates how light readings taken at different sensor locations of the microassembled imaging cytometer of FIG. 2 may vary as a function of time, in accordance with embodiments of the invention.
Figure 5B:
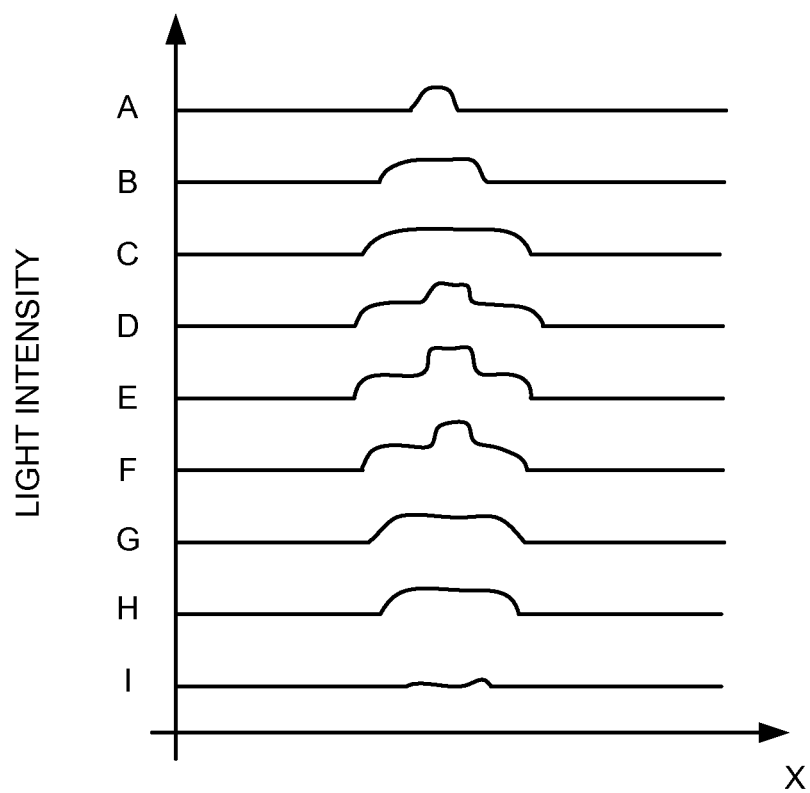
FIG. 5B shows the traces of FIG. 5A after spatial alignment.
Figure 6:
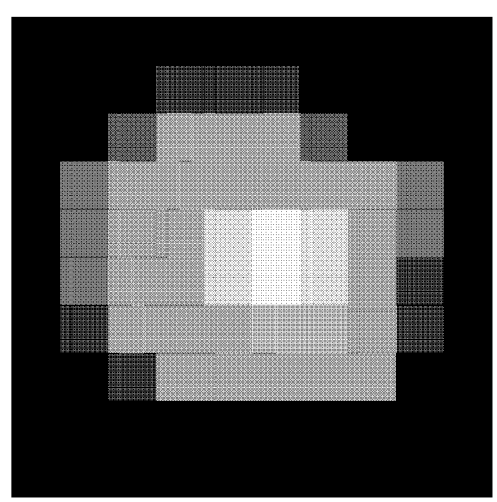
FIG. 6 shows a digital image constructed from the data of FIGS. 5A and 5B.

To construct a digital image of cell 101, system 200 takes a time-sequenced series of readings of the light falling on array light sensor 210. Locations on array light sensor 210 corresponding to the individual focused illumination spots 206 are identified and separately tracked. FIG. 5a illustrates how the light readings at the sensor locations corresponding to paths A-I may vary as a function of time as cell 101 traverses flow channel 201. As can be seen, cell 101 encounters illumination along path G first, and along the other paths at progressively later times, with path F being the last to receive light. Because the system geometry and the speed of travel of cell 101 are known, and the frequency at which readings are taken is known, the light intensity traces taken along paths A-G can be spatially aligned to form a digital image of cell 101. The spatially aligned traces are shown in FIG. 5B. The spatially aligned data may then be assembled into a digital image of cell 101, as shown in FIG. 6, in which a higher light intensity is shown in a lighter gray shade than is a lower light intensity. Of course, cytometers according to other embodiments may use different numbers of focused illumination spots 206, and may produce images of much higher resolution than that shown in FIG. 6.

In this example, more light emanated by fluorescence from a particular location on cell 101 results in a higher light intensity signal, so that portions of the cell carrying more fluorophore are represented as lighter in FIG. 6. This relationship could be reversed, if desired, so that portions of cell 101 emanating more light are represented as darker in the resulting digital image. If system 200 were to be used for direct imaging in the light wavelengths contained in beam 204 (without the benefit of fluorescence), cell 101 may be thought of as casting a shadow on array light sensor 210, so that denser parts of cell 101 would result in less light reaching array light sensor 210.

Figure 7:
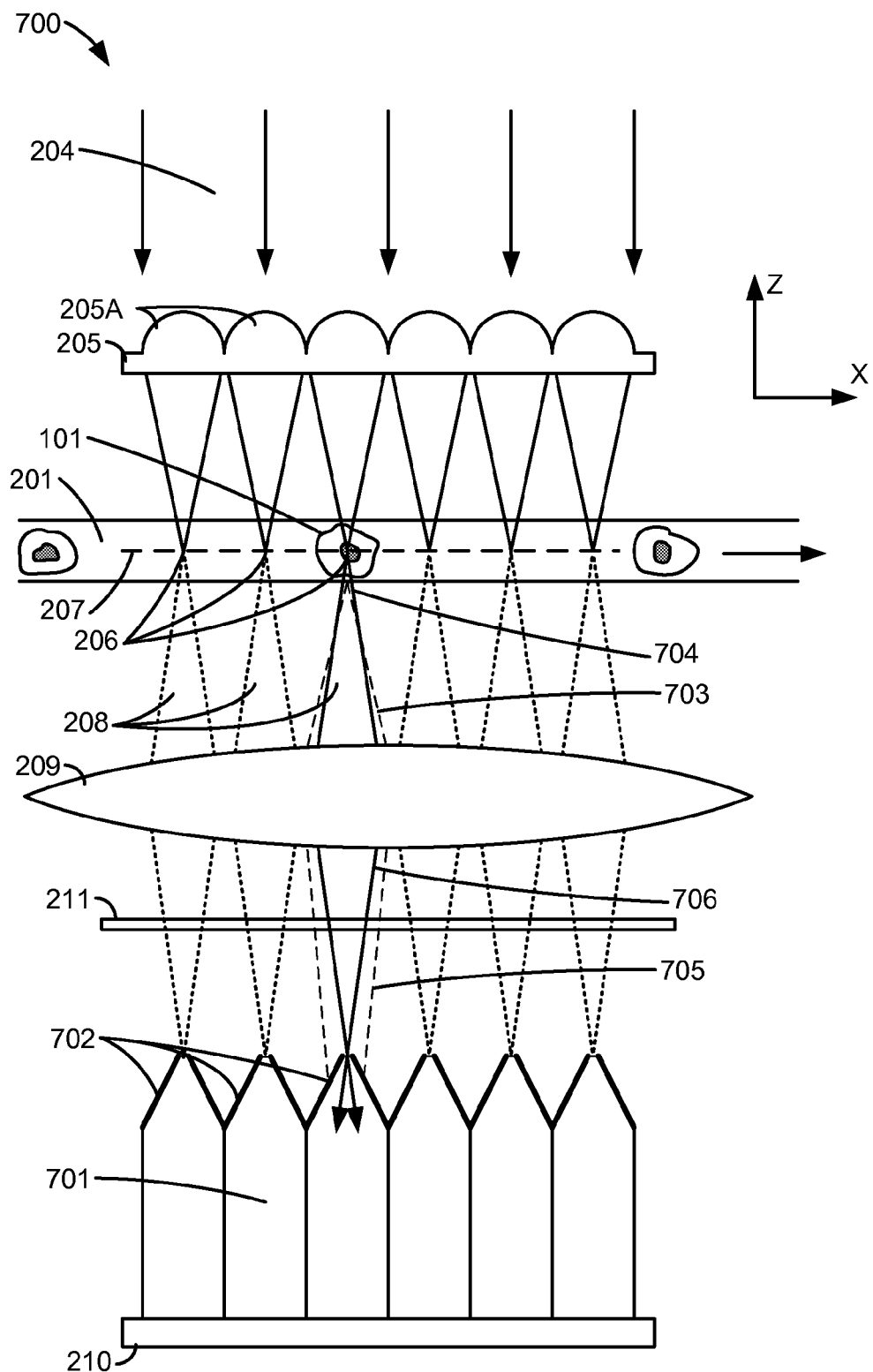
FIG. 7 illustrates a microassembled confocal imaging cytometer, in accordance with embodiments of the invention.

In some embodiments, the microassembled imaging cytometer may comprise an optical element near array light sensor 210 that configures the system to be substantially confocal. FIG. 7 illustrates a microassembled confocal imaging flow cytometer 700, in accordance with embodiments of the invention. Several of the components of system 700 are similar to those of system 200 discussed above, and are given the same reference labels as in system 200. System 700 is configured to be substantially confocal by the addition of an optical fiber bundle 701 near array light sensor 210. The tops 702 of the individual fibers in optical fiber bundle 701 are preferably configured to be opaque or reflective except for a narrow portion that admits light. For example, portions of the fibers may be coated with aluminum or gold plated 100 to 200 nanometers thick. The fibers then direct the admitted light to array light sensor 210. The ends 702 of the fibers thus act in a way similar to an aperture plate, to preferentially admit light emanating from sensing location 207, and preferentially exclude light emanating from other axial locations. For example, light emanating from illumination spots 206 at sensing location 207 and imaged by lens 209 follows a ray pencil such as pencil 706, and is tightly focused when it reaches the top surface of one of fibers 701, and is thus admitted by the fiber. Light emanating from a location below sensing location 207 may diverge in a pencil similar to pencil 703, to be converged by lens 209 into a pencil such as pencil 705. Pencil 705 has not converged to a tight spot by the time it reaches fibers 701, and is thus largely excluded by the opaque portion of the fiber ends. Similarly, light emanating from above sensing location 207 will have converged and re-diverged by the time it reaches fibers 207, and is thus also largely excluded by fibers 701. System 700 thus preferentially passes light emanating from sensing location 207 and preferentially blocks some light emanating from other axial locations.

Figure 8:
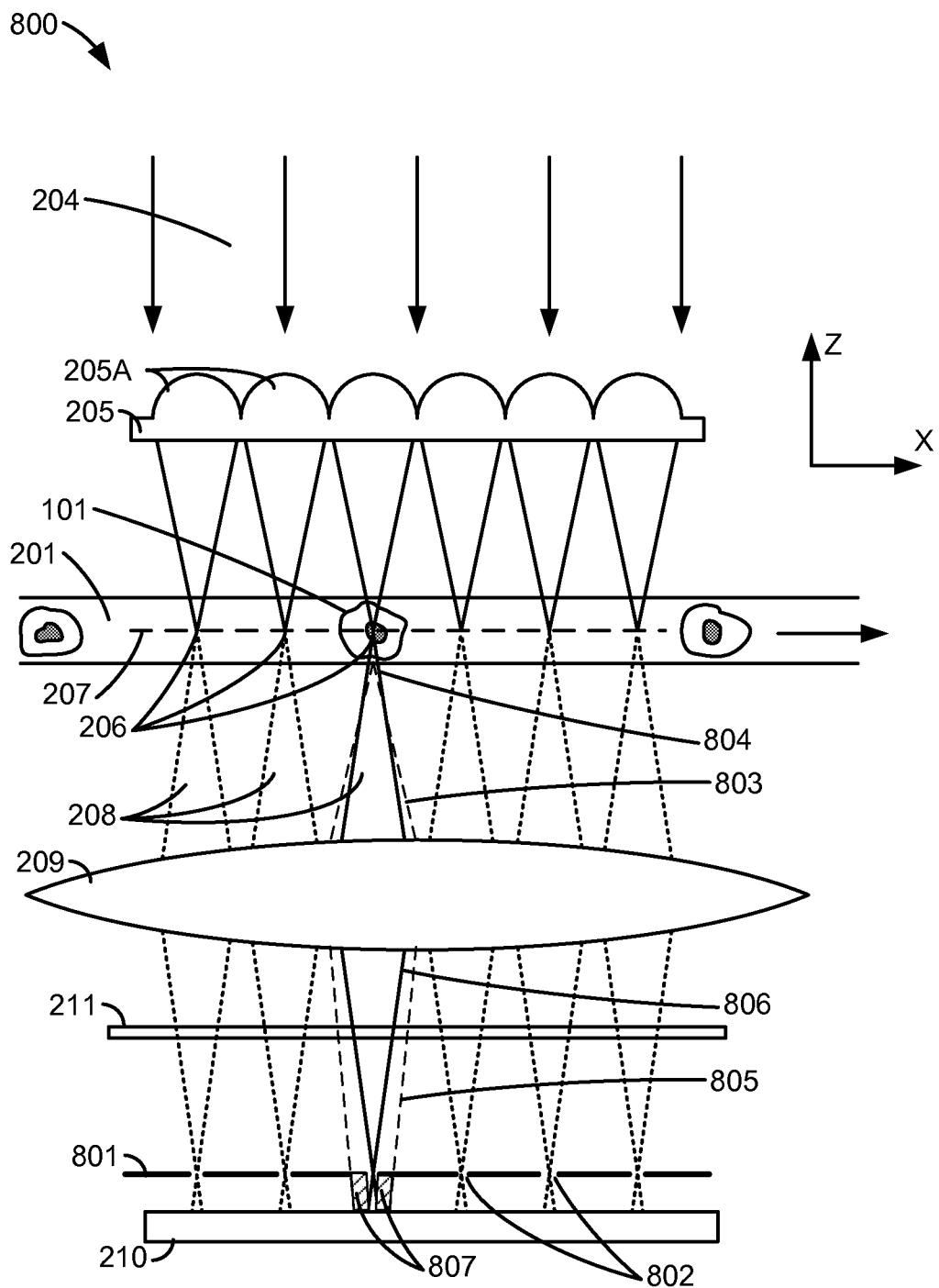
FIG. 8 illustrates a microassembled confocal imaging cytometer in accordance with other embodiments.

FIG. 8 illustrates a microassembled confocal imaging flow cytometer 800, in accordance with other embodiments. Several of the components of system 800 are similar to those of system 200 discussed above, and are given the same reference labels as in system 200. In addition, another optical component, aperture plate 801, is provided near the surface of array light sensor 210. Aperture plate 801 is substantially opaque, except for an array of apertures 802. Each aperture 802 corresponds to one of microlenses 205A, and is aligned to permit the passage of light emanating from the corresponding focused illumination spot 206. Optical element 801 configures system 800 to be substantially confocal. That is, apertures 802 have the effect of blocking light from axial locations other than those in sensing location 207. For example, ray pencil 803 emanates from location 804, well below sensing location 207. The resulting light is refocused by collection lens 209 into another ray pencil 805, more slowly converging than the pencil 806 originating from sensing location 207. Ray pencil 805 is therefore partially blocked by one of apertures 802, indicated by shaded areas 807. Because system 800 preferentially passes light emanating from sensing location 207 and preferentially blocks some light emanating from other axial locations, the system may produce images of higher contrast or resolution than a system that is not configured to be substantially confocal. Ideally, aperture plate 801 is placed at the focal location of lens 209, to allow apertures 802 to be very small and to discriminate effectively between light emanating from sensing location 207 and light emanating from axial locations other than at sensing location 207. Each ray bundle originating from one of focused illumination spots 206 may then have diverged slightly by the time it reaches array light sensor 210, and processing unit may evaluate the intensity of each ray bundle by summing the readings from several pixels of array light sensor 210.

Figure 9:
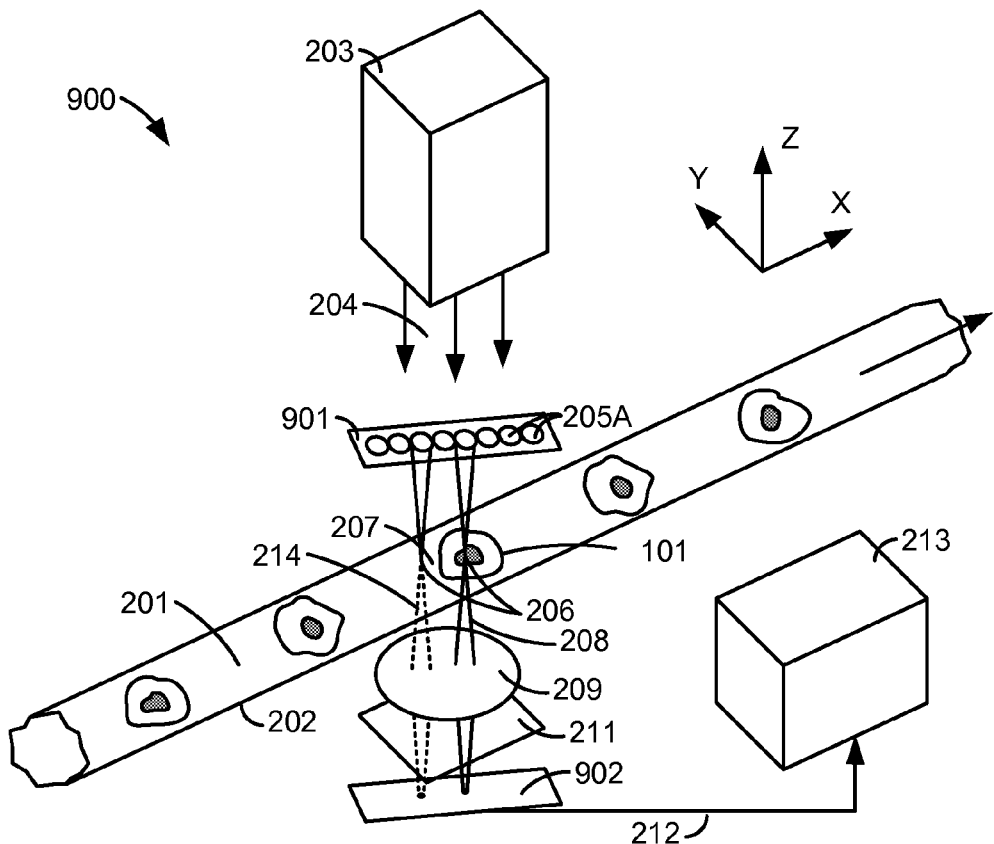
FIG. 9 illustrates a microassembled imaging cytometer in accordance with still other embodiments.
Figure 10:
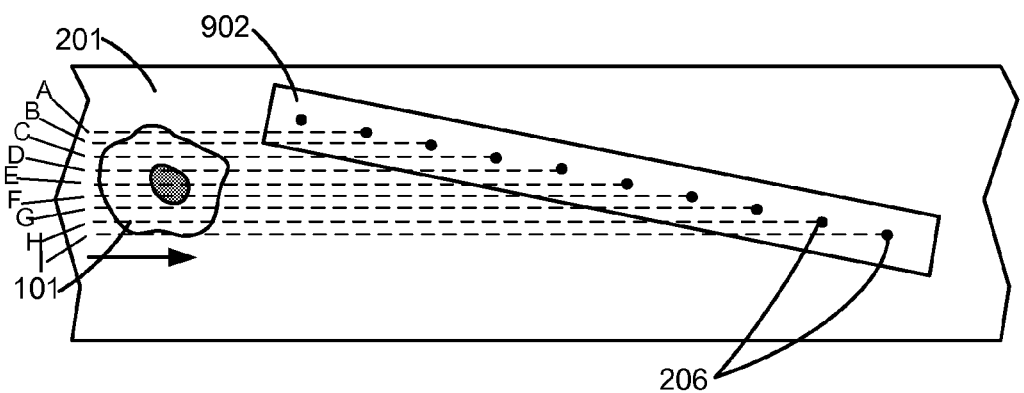
FIG. 10 illustrates the effect of a skew of some components in the microassembled imaging cytometer of FIG. 9.

FIG. 9 illustrates a microassembled confocal imaging flow cytometer 900 in accordance with other embodiments. In this embodiment, rather than a two-dimensional array of microlenses, a linear array 901 of microlenses 205A is used. Microlens array 901 is preferably skewed in relation to flow channel 201. Correspondingly, a linear array light sensor 902 is provided, and is also preferably skewed with respect to flow channel 201, and aligned with microlens array 901. Linear array light sensor 902 may comprise any suitable kind of sensor, including a CCD sensor, an EMCCD sensor, an APD, a PMT, a CMOS sensor, or another kind of sensor. FIG. 10 illustrates that even though the focused illumination spots 206 provided by microlens array 901 may be relatively widely spaced, the skewed arrangement ensures that a cell 101 traversing flow channel 201 will be well covered and relatively densely imaged during its traverse. The construction of a digital image of cell 101 by system 900 is analogous to the construction described above with respect to FIGS. 4-6. System 900 may also include one or more optical elements that configure system 900 to be substantially confocal, and may sense light emanating from cell 101 by fluorescence, or may perform direct imaging.

Figure 11:
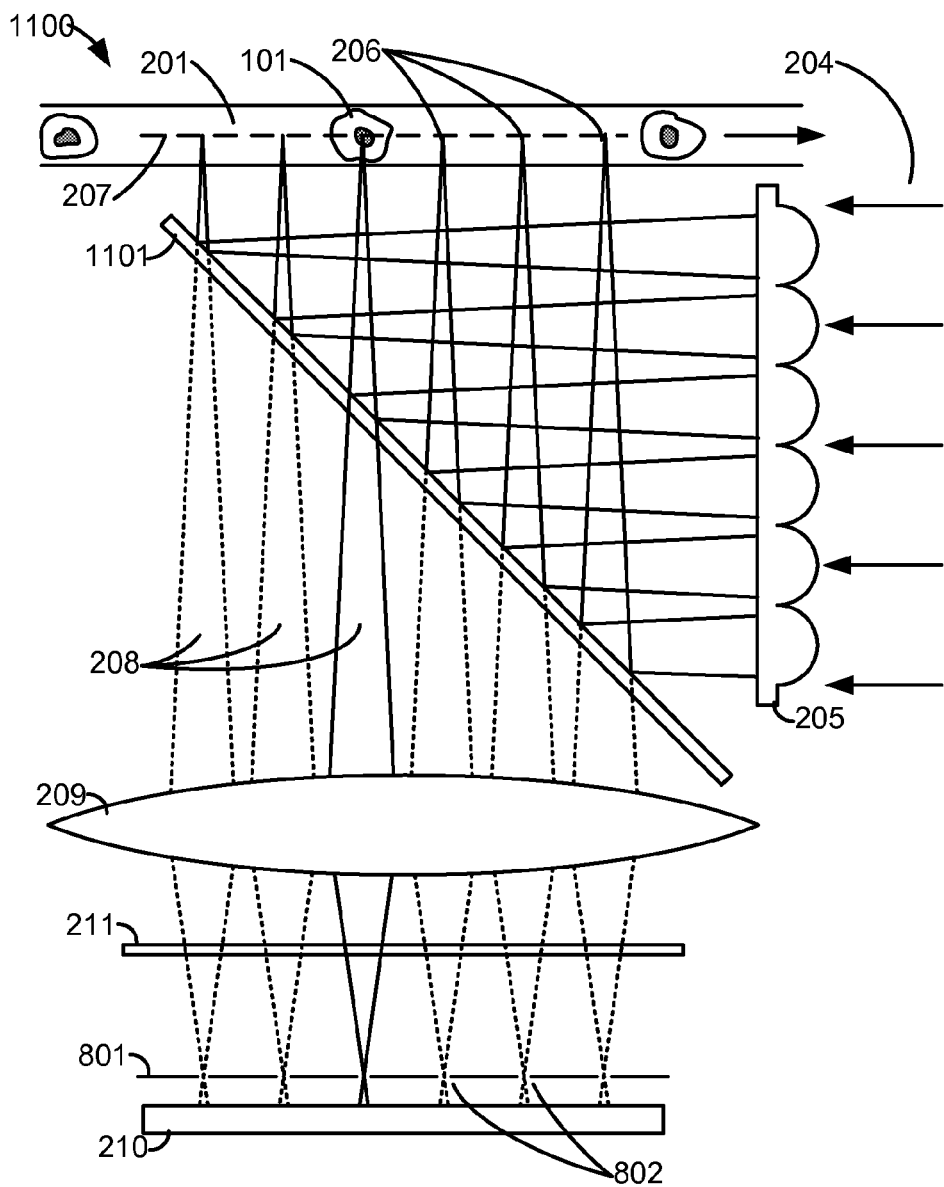
FIG. 11 illustrates a microassembled imaging cytometer in accordance with other embodiments, in which cells are illuminated and sensed from the same side of a sensing location.

FIG. 11 illustrates a microassembled confocal imaging flow cytometer 1100 in accordance with other embodiments. While system 200 described above illuminated and sensed cells from opposite sides of sensing location 207, microassembled imaging cytometer 1100 illuminates and senses cells from the same side of sensing location 207. In system 1100, light beam 204 is focused by focusing element 205 to a plurality of focused illumination spots 206. Focusing element 205 is illustrated as an array of microlenses, but may be any suitable focusing element. A wavelength-selective mirror 1101 redirects the light toward flow channel 201 such that the focused illumination spots are at sensing location 207. Mirror 1101 may be, for example, a dichroic mirror configured to reflect substantially all of the light incident on it from beam 204. Light 208 emanates from cell 101, and at least some of the emanating light 208 is collected and refocused by collection lens 209. System 1100 may be especially suited to imaging cells using light emanated by fluorescence, as wavelength-selective mirror 1101 can be configured to pass substantially all light in a wavelength band in which cells 101 emit light by fluorescence. An optional additional filter 211 may further condition the collected light 208, which is focused on array light sensor 210. Array light sensor 210 may be a two-dimensional array or a linear array, and may comprise any suitable kind of light sensor, including a CCD sensor, an EMCCD sensor, an APD, a PMT, a CMOS sensor, or another kind of sensor. System 1100 may include an optical element that configures the system to be substantially confocal, for example aperture plate 801 having apertures 802 or an optical fiber bundle. Construction of a digital image of cell 101 using system 1100 proceeds in a way similar to that described above with respect to system 200, and illustrated in FIGS. 4-6.

Figure 12:
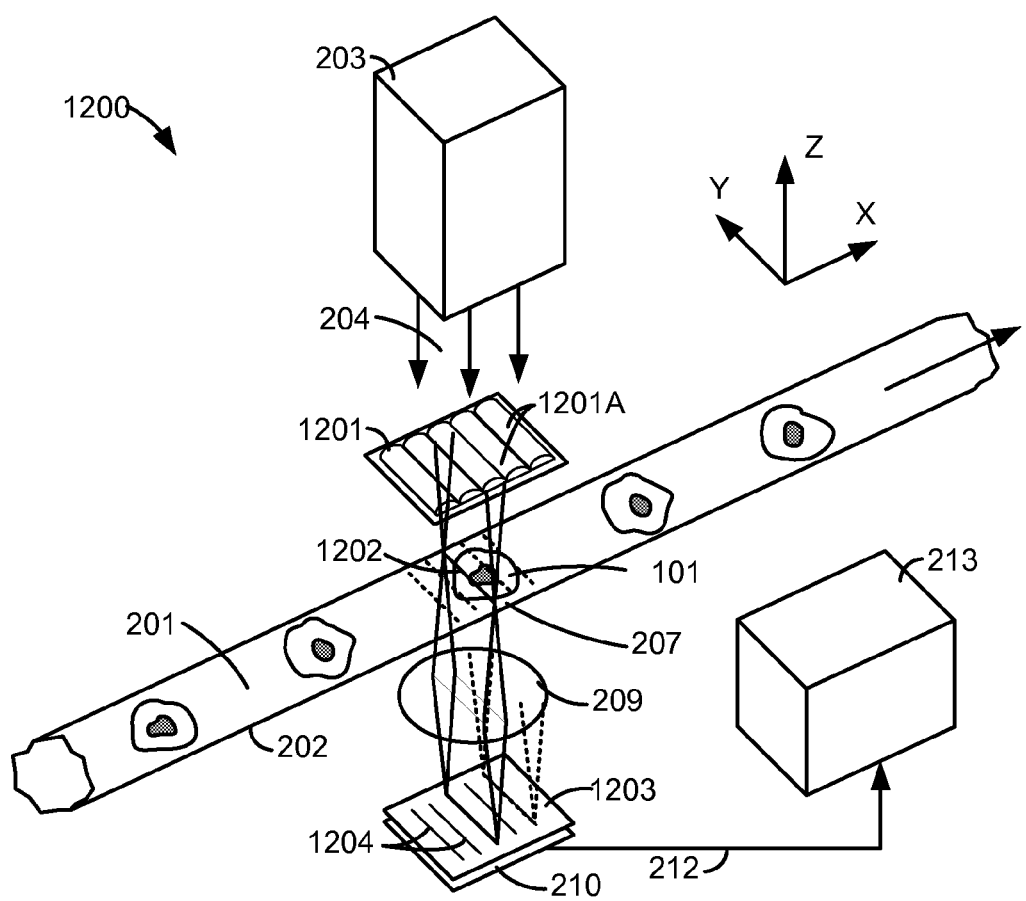
FIG. 12 illustrates a microassembled confocal imaging flow cytometer in accordance with other embodiments.

FIG. 12 illustrates a microassembled confocal imaging flow cytometer 1200 in accordance with other embodiments. Several of the components of system 1200 are similar to those of system 200 discussed above, and are given the same reference labels as in system 200. Cells such as cell 101 traverse flow channel 201, which is bounded by wall 202. A light source 203 produces light beam 204. Light source 203 may be, for example, a laser. A focusing element 1201 receives light from light source 203 and focuses the light. In contrast to focusing element 205 of system 200, focusing element 1201 is an array of cylindrical lenses 1201A or another kind of optical component that focuses light from beam 204 into a plurality of lines such as illumination line 1202, at or near sensing location 207 to illuminate the cells. Light emanating from a cell, whether by scattering or fluorescence, is collected and refocused by collection lens 209 at an aperture plate 1203. Aperture plate 1203 comprises a series of narrow slits 1204 aligned to receive the focused light from illumination lines 1202. Thus the system is confocal, in that it tends to reject light emanating from Z-axis locations away from sensing location 207. Light passing through aperture plate 1203 reaches light sensor 210. (Optional filters have been omitted from FIG. 12 for clarity.) Light sensor 210 produces signals indicating the intensity of light falling on the sensor, and the signals may be transmitted 212 to a processing unit 213 for storage, analysis, or display.

While system 1200 is illustrated producing illumination lines 1201 close enough together that several lines may fall on a single cell at once, this is not a requirement, and in fact it may be preferable that focusing element 1201 produce illumination lines spaced further apart than the expected size of a cell. Since cells are often widely spaced from each other in flow channel 201, having widely spaced illumination lines 1202 may result in light from only one illumination line and one cell reaching sensor 210 at any one time. In that arrangement, sensor 210 may be simplified, and could even be a simple photodiode, photomultiplier tube, or other kind of sensor that measures light intensity but does not include an array of pixels.

Figure 13:
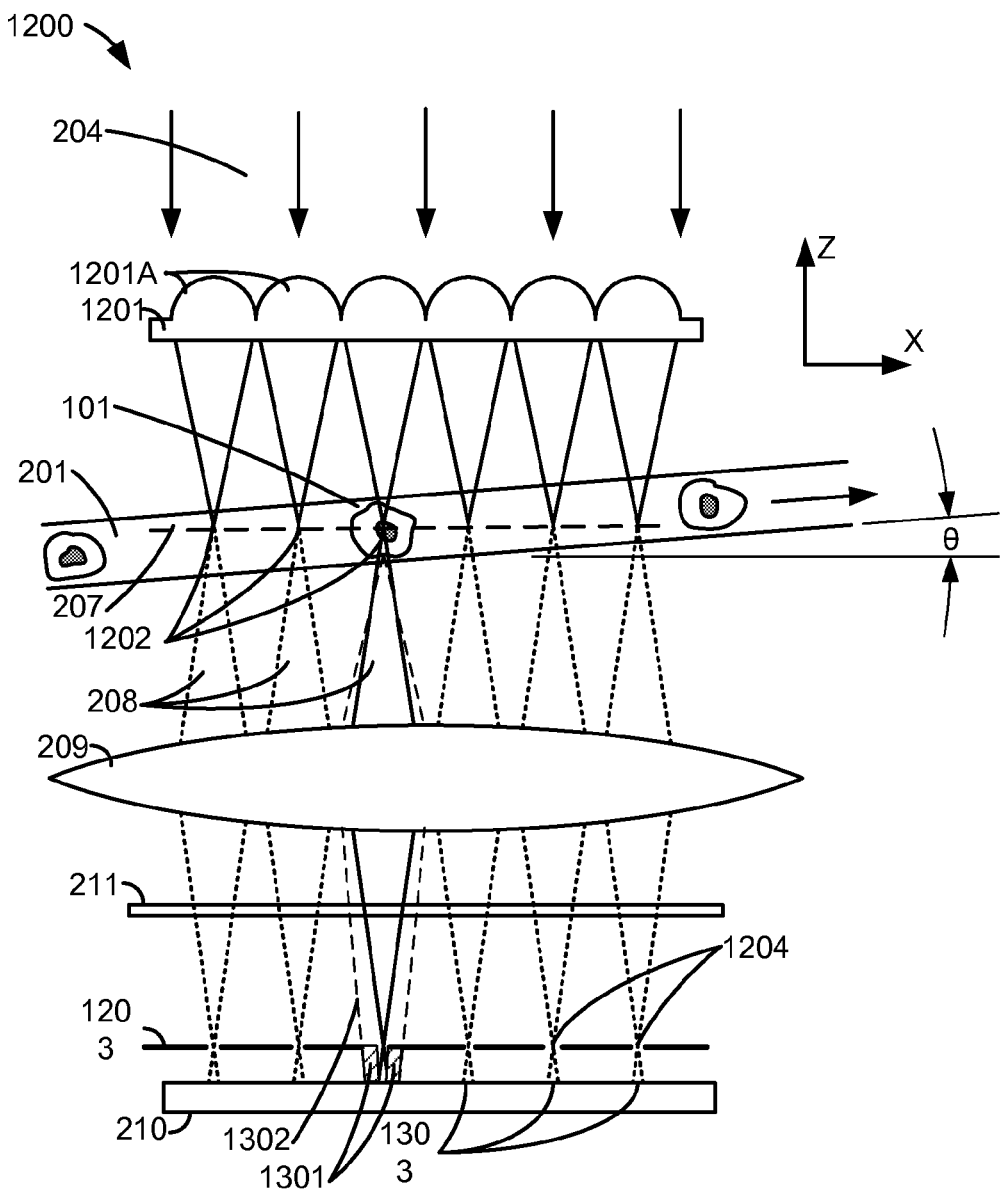
FIG. 13 shows an orthogonal view of the system of FIG. 12, in accordance with embodiments of the invention.

FIG. 13 shows an orthogonal view of system 1200, in accordance with embodiments of the invention. As can be seen, slits 1204 configure the system to be confocal, for example excluding portion 1301 of ray bundle 1302, which originated at a location displaced from sensing location 207.

FIG. 13 also shows another aspect of system 1200, in accordance with embodiments of the invention. Flow channel 201 is tilted in relation to sensing location 207. In FIG. 13, the tilt is shown by angle θ, which may be exaggerated as compared with actual practice for clarity of explanation. The tilt of flow channel 201 with respect to sensing location 207, in combination with the confocal aspect of system 1200, results in each oblong pool of light falling on sensor 210, exemplified by pools 1303, substantially originating from a unique Z-axis location with respect to cell 101.

Figure 14:
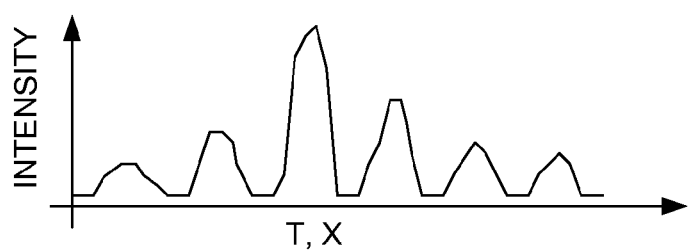
FIG. 14 illustrates a series of light intensity readings that may result from the traversal of one cell through the sensing area of the system of FIG. 12.

FIG. 14 illustrates a series of light intensity readings that may result from the traversal of one cell 101 through sensing area 207 of system 1200. The readings are take time-sequentially, so each reading indicates the intensity of light emanating from cell 101 at a particular time, which corresponds to a particular X location of cell 101, and also to a particular X location within the cell. For example, readings may be taken sufficiently often that cell 101 travels 0.25 to 0.5 micrometers between readings. Because flow channel 201 is tilted, each reading also corresponds to a particular Z location within the cell. FIG. 14 may represent a measurement of light emanating from cell 101 by fluorescence, as during times when cell 101 is between illumination lines, very low illumination levels are recorded. In the hypothetical example of FIG. 14, the highest intensity readings are obtained when the nucleus of cell 101 traverses one of illumination lines 1202. The combined readings give information about the structure of cell 101, at least in an X-Z cross section, even if sensor 210 is a single sensor without pixels. If sensor 210 does include an array of individual pixels, some structural information about the Y-direction structure of the cell may also be available. In some imaging applications using multicolor fluorescence imaging, it is desirable that a separate detector be provided for each fluorescence color.

While only six cylindrical lenses 1201A are shown in system 1200, one of skill in the art will recognize that other numbers could be used. For example, as many as 20 to 100 illumination lines may be generated. In one example embodiment, about 40 cylindrical lenses may be used, each having a radius of about 25 micrometers (a width of 50 micrometers), so that sensing area 207 is about 2 millimeters long in the X direction. If flow channel 201 has a height of about 50 micrometers, then the preferred tilt of flow channel 201 with respect to sensing location 207 is about θ=50/2000=0.025 radians. Other suitable tilt angles are possible, depending on the height of the flow channel and number and size of the microlenses used.

One of skill in the art will recognize that a system could also be constructed that uses a focusing element similar to focusing element 1201 to form lines of illumination at sensing location 207, and also illuminates and senses cells from the same side, similar to the way illumination and sensing are accomplished in system 900, shown in FIG. 9.

Figure 15:
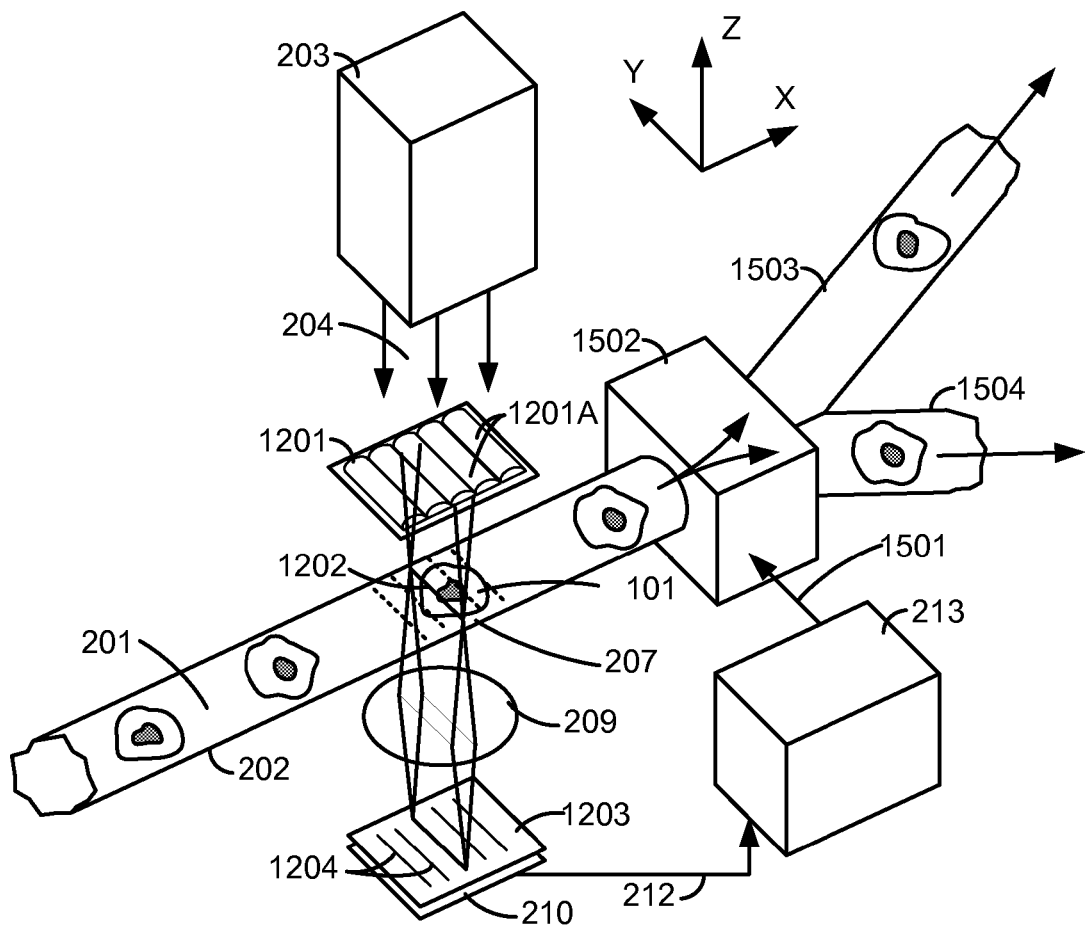
FIG. 15 shows a detection and analysis system be coupled with a sorting mechanism, in accordance with embodiments of the invention.

In accordance with other embodiments of the invention, the results of an analysis performed by processing unit 213 may be used to sort cells. For example, processing unit 213 may analyze signals produced by sensor 210 or 902 to decide if particular cells are circulating tumor cells. Circulating tumor cells may be characterized by particular measurements of cell size, nucleus size, and ratio of nucleus to cytoplasm, all of which may be detectable using systems in accordance with embodiments of the invention. The detection and analysis system may be coupled with a sorting mechanism to isolate particular cells meeting certain detection criteria. Such a system is illustrated in FIG. 15, using system 1200 as the example detection means. Based on the analysis of a particular cell, processing unit 213 may be able to classify the cell and send a signal 1501 to a sorting unit 1502, that directs each cell to one of two channels 1503, 1504 for collection. For example, sorting unit 1502 may include a piezoelectric or optical force element for redirecting the paths of individual cells.

While embodiments of the invention have been illustrated as scanning cells confined in a linear tube, one of skill in the art will recognize that embodiments of the invention may be utilized in systems using any of a wide range of cell delivery techniques, including electrophoresis, pressure driven flow, optical tweezers, motorized translation stage, and others. Cells may be conveyed as a payload in an oil emulsion, in an electrowetting-actuated droplet, or via magnetic transport assisted by magnetic bead tagging. Relative motion between a cell and the sensing location could be provided by mechanical movement of a slide that carries the cell, by movement of components of the cytometer while the cell remains stationary, or by relative motion when the cell and cytometer components move at different speeds or in different directions. It is intended that the claims not be limited by the cell delivery method utilized.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A microassembled imaging cytometer, comprising:
    a sensing location that undergoes relative motion with a cell;
    a light source that produces a beam;
    a focusing element, the focusing element focusing light from the beam of light to a plurality of focused illumination spots at a focal plane at the sensing location, such that the cell is illuminated by one or more of the focused illumination spots as the cell traverses the sensing location, wherein each of the focused illumination spots is smaller than the cell;
    an array light sensor that comprises an array of pixels and produces signals indicating the intensity and distribution of light falling on the pixels;
    a collection lens that collects and refocuses light emanating from the cell to a plurality of separate, discernible spots on the array light sensor; and
    a processing unit that constructs a digital image of the cell based at least in part on the signals.

2. The microassembled imaging cytometer of claim 1, further comprising a flow channel through which the cell is transported by a flowing fluid, the flow channel at least partially bounded by a wall that has at least a portion that is substantially transparent.

3. The microassembled imaging cytometer of claim 1, wherein the relative motion results at least in part from movement of the cell.

4. The microassembled imaging cytometer of claim 1, wherein the relative motion results at least in part from movement of a portion of the cytometer.

5. The microassembled imaging cytometer of claim 1, wherein the cell is attached to a slide, and wherein the relative motion results at least in part from movement of the slide.

6. The microassembled imaging cytometer of claim 1, wherein illumination of the cell is performed from a side of the sensing location, and sensing of the light emanating from the cell is performed from the same side of the sensing location.

7. The microassembled imaging cytometer of claim 1, wherein illumination of the cell is performed from a side of the sensing location, and sensing of the light emanating from the cell is performed from a different side of the sensing location.

8. The microassembled imaging cytometer of claim 1, wherein the focusing element comprises an array of microlenses having spherical surfaces.

9. The microassembled imaging cytometer of claim 1, wherein the focusing element comprises an array of microlenses having aspheric surfaces.

10. The microassembled imaging cytometer of claim 1, wherein the focusing element comprises at least one diffractive element.

11. The microassembled imaging cytometer of claim 1, wherein the light source comprises a laser.

12. The microassembled imaging cytometer of claim 1, wherein the processing unit constructs the digital image of the cell in part by spatially correlating light intensity readings taken from different parts of the cell at different times.

13. The microassembled imaging cytometer of claim 12, wherein correlating the light intensity readings taken from different parts of the cell at different times is performed at least in part based on a speed at which the cell traverses the sensing location.

14. The microassembled imaging cytometer of claim 1, wherein the focusing element comprises a linear array of microlenses.

15. The microassembled imaging cytometer of claim 1, wherein the focusing element comprises a two-dimensional array of microlenses.

16. The microassembled imaging cytometer of claim 1, wherein the array light sensor comprises a linear array of pixels.

17. The microassembled imaging cytometer of claim 1, wherein the array light sensor comprises a two-dimensional array of pixels.

18. The microassembled imaging cytometer of claim 1, further comprising at least one optical filter between the sensing location and the array light sensor.

19. The microassembled imaging cytometer of claim 1, wherein the array light sensor comprises at least one sensor selected from the group consisting of a charge coupled device sensor, an electron multiplying charge coupled device sensor, an avalanche photodiode sensor, a photomultiplier tube, and a complementary metal oxide semiconductor sensor.

20. The microassembled imaging cytometer of claim 1, wherein the plurality of focused illumination spots form an array of focused illumination spots, the array being skewed in relation to the motion of the cell and the sensing location.

21. The microassembled imaging cytometer of claim 1, further comprising an optical element proximate the array light sensor, the optical element configuring the microassembled imaging cytometer to preferentially admit light emanating from the sensing location and to preferentially block light emanating from other axial locations.

22. The microassembled imaging cytometer of claim 21, wherein the optical element comprises an array of microapertures.

23. The microassembled imaging cytometer of claim 21, wherein the optical element comprises a bundle of optical fibers.

24. The microassembled imaging cytometer of claim 1, wherein the collection lens collects and refocuses light emanating from the cell by fluorescence.

25. A method of performing cytometry, the method comprising:
    generating a light beam using a light source;
    focusing, using a focusing element, light from the light beam to a plurality of focused illumination spots at a focal plane at a sensing location that undergoes relative motion with a cell, wherein the size of each focused illumination spot is smaller than the cell;
    collecting and refocusing, using a collection lens separate from the focusing element, light emanating from the cell to a plurality of separate, discernable spots on an array light sensor;
    producing signals from the array light sensor indicating the intensity and distribution of light falling on the array light sensor; and
    constructing, using a processing unit, a digital image of the cell based at least in part on the signals from the array light sensor.

26. The method of claim 25, further comprising converting the signals to numerical values representing a pattern of light falling on the array light sensor.

27. The method of claim 25, wherein constructing a digital image of the cell further comprises:
    taking a time-sequenced series of readings of the light falling on the array light sensor;
    separately tracking light readings from the array light sensor corresponding to the individual focused illumination spots; and
    spatially aligning the separate light readings based at least in part on a known system geometry, a speed of travel of the cell, and a frequency at which light readings are taken.

28. The method of claim 25, further comprising filtering the light emanating from the cell to selectively block light in wavelengths emitted by the light source and to selectively pass light in wavelengths emanating from the cell by fluorescence.

29. The method of claim 25, further comprising providing an optical element proximate the array light sensor, the optical element configuring the microassembled imaging cytometer to preferentially admit light emanating from the sensing location and to preferentially block light emanating from other axial locations.

30. A microassembled imaging cytometer, comprising:
    a sensing location that undergoes relative motion with a cell;
    a light source that produces a beam of light;
    a focusing element, the focusing element focusing light from the beam to a plurality of focused illumination lines at the sensing location, such that the cell is illuminated by one or more of the focused illumination lines as the cell traverses the sensing location;
    a light sensor; and
    a collection lens that collects and refocuses light emanating from the cell onto the array light sensor.

31. The microassembled imaging cytometer of claim 30, wherein the light sensor comprises an array of pixels.

32. A microassembled imaging cytometer, comprising:
    a sensing location that undergoes relative motion with a cell;
    a light source that produces a beam of light;
    a focusing element, the focusing element focusing light from the beam to a plurality of focused illumination spots or lines at a focal plane at the sensing location, such that the cell is illuminated by one or more of the focused illumination spots or lines as the cell traverses the sensing location and each focused illumination spot or line is smaller in at least one dimension than the cell;
    an array light sensor;
    a collection lens that collects and refocuses light emanating from the cell to a plurality of separate, discernible spots or lines on the array light sensor;
    a processing unit that analyzes signals from the light sensor to classify a cell; and
    a sorting mechanism that directs the classified cell to one of at least two collection channels.

33. The microassembled imaging cytometer of claim 1, wherein the optical resolution of the imaging cytometer is set primarily by the size of the focused illumination spots.

34. The method of claim 25, wherein the optical resolution of a system performing the method is set primarily by the size of the focused illumination spots.

* * * * *